(12) United States Patent
Lee et al.

(10) Patent No.: US 11,006,916 B2
(45) Date of Patent: May 18, 2021

(54) APPARATUS AND METHOD FOR K-EDGE BASED INTERIOR TOMOGRAPHY IMAGE PROCESSING

(71) Applicants: Pusan National University Industry-University Cooperation Foundation, Busan (KR); RENSSELAER POLYTECHNIC INSTITUTE, Troy, NY (US)

(72) Inventors: Seungwook Lee, Busan (KR); Ohsung Oh, Busan (KR); Ge Wang, Troy, NY (US)

(73) Assignees: Pusan National University Industry-University Cooperation Foundation, Busan (KR); Rensselaer Polytechnic Institute, Tory, NY (US)

( * ) Notice: Subject to any disclaimer, the term of this patent is extended or adjusted under 35 U.S.C. 154(b) by 1107 days.

(21) Appl. No.: 15/452,802

(22) Filed: Mar. 8, 2017

(65) Prior Publication Data
US 2018/0185001 A1 Jul. 5, 2018

(30) Foreign Application Priority Data

Jan. 5, 2017 (KR) .................. 10-2017-0001916

(51) Int. Cl.
*A61B 6/00* (2006.01)
*A61B 6/03* (2006.01)

(52) U.S. Cl.
CPC ........... *A61B 6/5211* (2013.01); *A61B 6/032* (2013.01); *A61B 6/4241* (2013.01); *A61B 6/469* (2013.01); *A61B 6/481* (2013.01); *A61B 6/504* (2013.01); *A61B 6/5205* (2013.01)

(58) Field of Classification Search
CPC combination set(s) only.
See application file for complete search history.

(56) References Cited

U.S. PATENT DOCUMENTS

2011/0282181 A1* 11/2011 Wang .................. A61B 6/4007
600/407

* cited by examiner

Primary Examiner — Joel F Brutus
(74) Attorney, Agent, or Firm — Rabin & Berdo, P.C.

(57) ABSTRACT

Provided are an apparatus and method for K-edge based interior tomography image processing. The apparatus efficiently performs tomography image reconstruction by acquiring different material images using an energy-selective detector, such as a photon counting detector. The apparatus includes a projection image acquisition unit configured to inject a contrast agent into an object and acquire projection images using the energy-selective detector with respect to a K-edge of the material, a parameter initialization unit configured to initialize parameters needed for image reconfiguration, an ROI interior reconstruction unit configured to perform reconstruction for image reconfiguration until initial convergence is achieved in order to reconstruct an interior of a region of interest, a concentration and correction value calculation unit configured to calculate a concentration and a correction value (β) using a linear attenuation coefficient of the contrast agent and a linear attenuation coefficient of blood, which are known, in the acquired and reconstructed image.

14 Claims, 6 Drawing Sheets

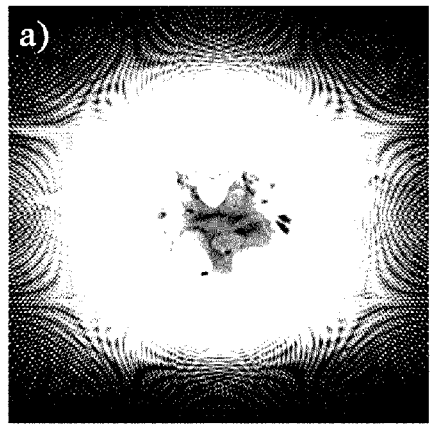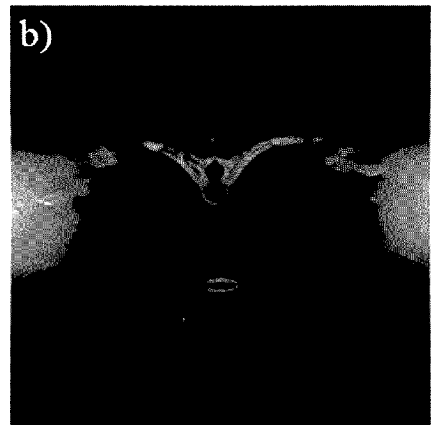
FIG. 6A    FIG. 6B
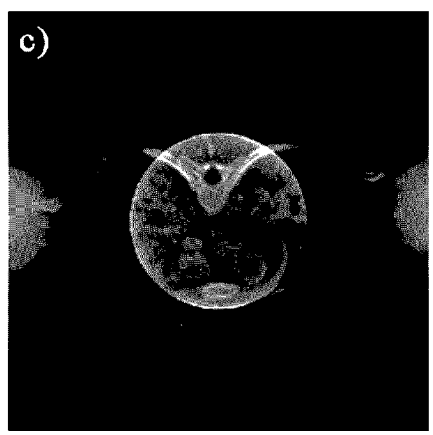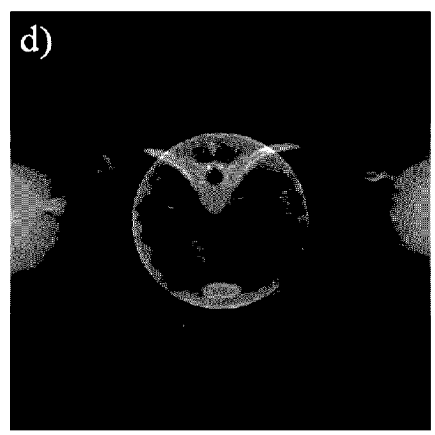
FIG. 6C    FIG. 6D

APPARATUS AND METHOD FOR K-EDGE BASED INTERIOR TOMOGRAPHY IMAGE PROCESSING

CROSS-REFERENCE TO RELATED APPLICATION(S)

This application claims priority from Korean Patent Application No. 10-2017-0001916, filed on Jan. 5, 2017, in the Korean Intellectual Property Office, the disclosure of which is incorporated herein by reference in its entirety.

BACKGROUND

1. Field

The following description relates to tomography image processing, and more particularly, to a K-edge based interior tomography image processing apparatus and method that may efficiently perform tomography image reconstruction by acquiring different material images using an energy-selective detector, such as a photon counting detector.

2. Description of Related Art

X-rays are used as one of the effective methods for acquiring a tomography image of an object without destroying the object in medical and industrial fields.

Generally, in order to acquire a tomography image of an object using radiation such as X-rays, the radiation needs to cover the whole object.

Accordingly, when a tomography image of a huge object is intended to be acquired, a very large radiation imaging system is necessary. In order to solve this problem, interior tomography technology capable of reconstructing a region of interest (ROI) inside an object has been developed.

FIGS. 1A and 1B show a difference in image acquisition between (FIG. 1A) a tomography technique and (FIG. 1B) interior tomography.

Since only an ROI inside an object may be reconstructed when the interior tomography method is used, there are many advantages in that an image can be quickly acquired, a system can be reduced in size, a large object can be used, etc., compared to the tomography technique.

Theoretically, the conventional internal tomography has no method of exactly reconstructing an ROI inside an object.

However, on the assumption that some information is known, that is, if an internal value (i.e., a sub-region) of an ROI is known or if an ROI is piecewise-constant or piecewise-polynomial (i.e., a sparsity model), the ROI can be exactly reconstructed.

In this case, the following problems are present.

(1) When an actual image is acquired, a sub-region inside an object cannot be known.

(2) An actual object is not a sparsity model.

(3) It is difficult to acquire an accurate image when an ROI inside an object is reduced.

Also, in the case of conventional technology, it is impossible to check an image difference according to x-ray energy because all x-ray energy values are summed and output.

Accordingly, there is a need to develop a new tomography reconstruction technique in order to solve these problems.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The following description relates to a K-edge based interior tomography image processing apparatus and method that may efficiently perform tomography image reconstruction by acquiring different material images using an energy-selective detector such as a photon counting detector capable of classifying x-rays according to energy.

The following description also relate to a K-edge based interior tomography image processing apparatus and method that may use images on both sides of a K-edge of a material (low-energy region and high-energy region) in order to reconstruct an internal image of the object using the K-edge of the material and an energy-selective detector, such as a photon counting detector.

The following description also relates to a K-edge based interior tomography image processing apparatus and method that may increase image reconfiguration performance by injecting a material (contrast agent) with a known value into an object, reconstructing an interior of the object using a linear attenuation coefficient of the material that changes depending on a left or right side of a K-edge, performing multiplication of a ratio between the known value of the material and a value acquired through the image reconstruction, and compensating for an internal value of the object.

The following description also relates to a K-edge based interior tomography image processing apparatus and method that may increase image reconfiguration performance by injecting a material (contrast agent) with a known value into an object, reconstructing an interior of the object using a linear attenuation coefficient of the material that changes depending on a left or right side of a K-edge, performing addition of a difference between the known value of the material and a value acquired through the image reconstruction, adjusting the sum to a known value, and performing image reconstruction.

The present invention is not limited to the above objectives, but other objectives may be clearly understood by those skilled in the art from the following description.

In one general aspect, an apparatus for K-edge based interior tomography image processing includes a projection image acquisition unit configured to inject a contrast agent into an object and acquire projection images using an energy-selective measurement method with respect to a K-edge of the material; a parameter initialization unit configured to initialize parameters needed for image reconfiguration; an ROI interior reconstruction unit configured to perform reconstruction for image reconfiguration until initial convergence is achieved in order to reconstruct an interior of a region of interest (ROI); a concentration and correction value calculation unit configured to calculate a concentration and a correction value ($\beta$) using a linear attenuation coefficient of the contrast agent and a linear attenuation coefficient of blood, which are known, in the acquired and reconstructed image; an image compensation unit configured to compensate for the image by using the correction value ($\beta$) calculated by the concentration and correction value calculation unit; an iterative reconfiguration determination unit configured to make a determination for stopping iterative reconfiguration when a maximum number of iterations are achieved or the correction value ($\beta$) converges, and a reconfigured image and concentration output unit configured to output a resultant image obtained using an iterative reconfiguration and compensation method and also output a concentration ($\alpha$) at that time.

The projection image acquisition unit may use an energy-selective detector, such as a photon counting detector, in order to acquire the projection images with respect to the K-edge using the energy-selective measurement method.

When the contrast agent is injected into the object, a contrast agent value (L) on the left side of the K-edge and a contrast agent value (R) on the right side of the K-edge may be calculated using the following equations:

$$L = \alpha I_L + (1-\alpha) B_L$$

$$R = \alpha I_R + (1-\alpha) B_R$$

where $I_L$ is a linear attenuation coefficient of the contrast agent on the left side of the K-edge, $B_L$ is a linear attenuation coefficient of the blood on the left side of the K-edge, $I_R$ is a linear attenuation coefficient of the contrast agent on the right side of the K-edge, and $B_R$ is a linear attenuation coefficient of the blood on the right side of the K-edge.

A linear attenuation coefficient that is an image value may be determined by a density ratio between the contrast agent and the blood.

The contrast agent may be iodine having a K-edge at an energy value of 33.2 keV or barium having a K-edge at an energy value of 37.4 keV.

The ROI interior reconstruction unit may perform reconstruction for image reconfiguration using SART+TV minimization until initial convergence is achieved in order to reconstruct the interior of the ROI.

The reconfigured image and concentration output unit may output a left K-edge image obtained by imaging a low-energy area and a right K-edge image obtained by imaging a high-energy area with respect to the k-edge, which is an energy boundary at which there is a sudden increase in the linear attenuation coefficient.

The image compensation unit may reconstruct an interior of the object using a linear attenuation coefficient of the material that changes depending on a left or right side of the K-edge and may perform multiplication of a ratio of a known value of the material and a value acquired through image reconstruction to compensate for an internal value of the material.

The image compensation unit may reconstruct an interior of the object using a linear attenuation coefficient of the material that changes depending on a left or right side of the K-edge and may perform addition of a difference between a known value of the material and a value acquired through image reconstruction and adjust the sum to a known value to perform image reconstruction.

In another general aspect, a method for K-edge based interior tomography image processing includes a projection image acquisition operation of injecting a contrast agent into an object and acquiring projection images using an energy-selective measurement method with respect to a K-edge of the material, a parameter initialization operation of initializing parameters needed for image reconfiguration, an ROI interior reconstruction operation of performing reconstruction for image reconfiguration until initial convergence is achieved in order to reconstruct an interior of a region of interest (ROI), a concentration and correction value calculation operation of calculating a concentration and a correction value ($\beta$) using a linear attenuation coefficient of the contrast agent and a linear attenuation coefficient of blood, which are known, in the acquired and reconstructed image, an image compensation operation of compensating for the image using the calculated correction value ($\beta$); an iterative reconfiguration determination operation of making a determination for stopping iterative reconfiguration when a maximum number of iterations are achieved or the correction value ($\beta$) converges; and a reconfigured image and concentration output operation of outputting a resultant image obtained using an iterative reconfiguration and compensation method and also output a concentration ($\alpha$) at that time.

Other features and aspects will be apparent from the following detailed description, the drawings, and the claims.

BRIEF DESCRIPTION OF THE DRAWINGS

FIGS. 6A through 6D show an image configuration diagram obtained through K-edge based interior tomography image processing according to the present invention.

Figure 1A:
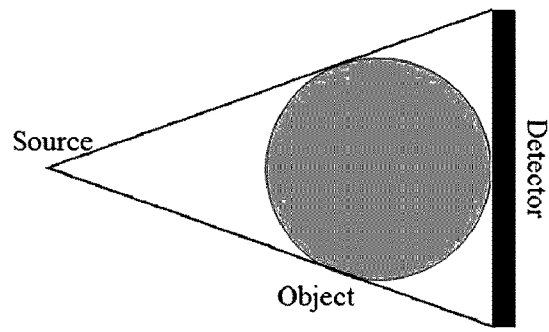
FIGS. 1A and 1B show a difference in image acquisition between (FIG. 1A) a tomography technique and (FIG. 1B) interior tomography.
Figure 1B:
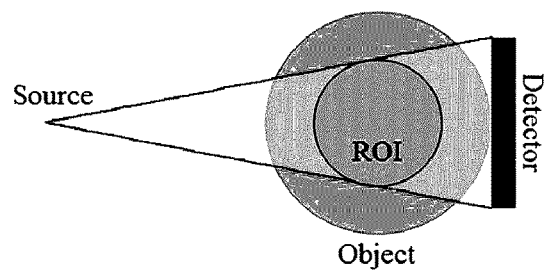

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, example embodiments of an apparatus and method for K-edge based interior tomography image processing according to the present invention will be described in detail as follows.

The features and advantages of the apparatus and method for K-edge based interior tomography image processing according to the present invention will become apparent from the detailed description of the following embodiments.

Figure 2:
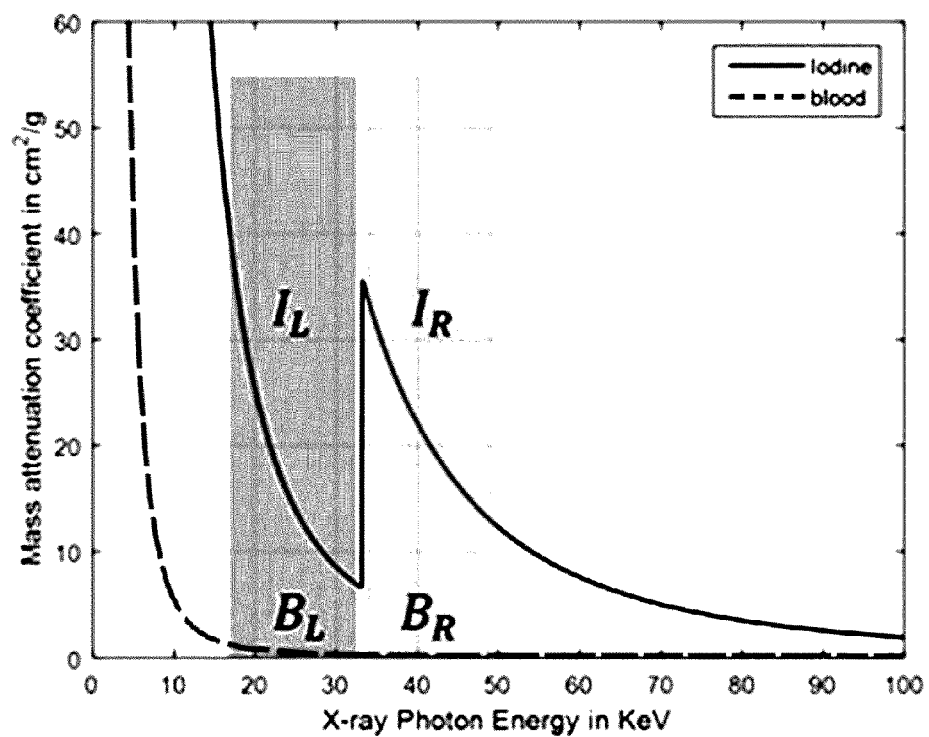
FIG. 2 is a graph showing linear attenuation coefficients of a contrast agent (iodine) and another material (blood) with respect to x-ray energy.
Figure 3:
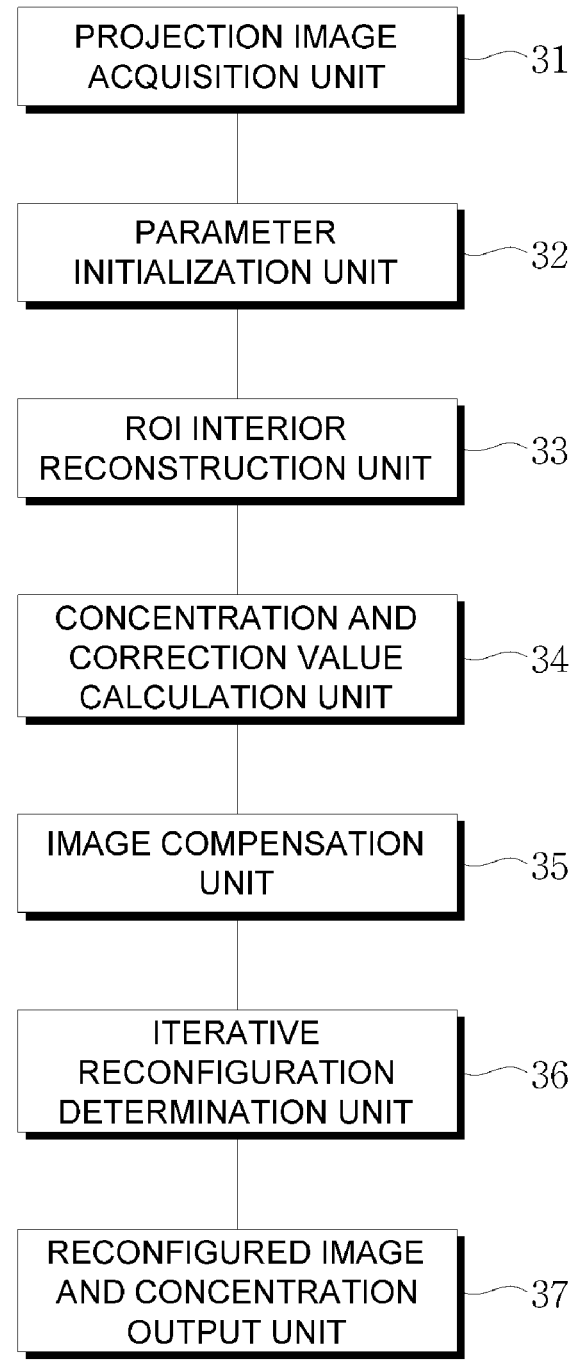
FIG. 3 is a block diagram showing an apparatus for K-edge based interior tomography image processing according to the present invention.

FIG. 2 is a graph showing a linear attenuation coefficient of contrast agent (iodine) and other material (blood) with respect to x-ray energy, and FIG. 3 is a block diagram showing an apparatus for K-edge based interior tomography image processing according to the present invention.

According to the present invention, it is possible to enhance image reconfiguration performance by reconstructing an internal image of an object using an energy-selective detector, such as a photon counting detector, and images on both sides of a K-edge of a material (low-energy region and high-energy region).

Also, according to the present invention, it is possible to enhance image reconfiguration performance by injecting a material (contrast agent) with a known value into an object, reconstructing an interior of the object using a linear attenuation coefficient of the material that changes depending on a left or right side of a K-edge, performing multiplication of a ratio between the known value of the material and a value acquired through the image reconstruction, and compensating for an internal value of the object.

Also, according to the present invention, it is possible to enhance image reconfiguration performance by injecting a material (contrast agent) with a known value into an object, reconstructing an interior of the object using a linear attenuation coefficient of the material that changes depending on a left or right side of a K-edge, performing addition of a difference between the known value of the material and a value acquired through the image reconstruction, and adjusting the sum to a known value to perform the image reconstruction.

"K-edge" used in the description of the apparatus and method for K-edge based interior tomography image processing according to the present invention may described as follows.

An X-ray linear attenuation coefficient of a material is a function of energy.

There is an energy boundary, that is, a specific x-ray energy value at which there is a sudden increase in the x-ray linear attenuation coefficient. The energy boundary is called K-edge.

This is caused by the binding energy of an electron, and there are several sections such as a k-edge, L-edge, etc., depending on the shell of an electron interacting with a photon.

Since an interaction probability rapidly increases at a part where energy of a photon is just above the binding energy of an electron, such boundaries are generated.

A left K-edge image refers to an image obtained by capturing a low-energy region with respect to the K-edge energy boundary, and a right K-edge image refers to an image obtained by capturing a high-energy region with respect to the K-edge energy boundary.

Since a difference between a left K-edge image and a right K-edge image is significant at a point where there is a K-edge contrast agent, and a difference in attenuation caused by x-rays is insignificant at a point where there is no K-edge contract agent, this fact is utilized for image correction.

The apparatus and method for K-edge based interior tomography image processing according to the present invention have been described as using iodine or barium as the contrast agent. However, the present invention is not limited thereto. As long as any material has a linear attenuation coefficient that significantly changes at a specific energy area such as a K-edge, the material can be used as the contrast agent.

Iodine has a K-edge at an energy value of 33.2 keV, and barium has a K-edge at an energy value of 37.4 keV. These energy areas are mainly used for radiation for diagnosis.

A known internal value (i.e., a known sub-region) of an ROI is an area that is already known before capturing. The internal value may be known as prior knowledge or may be captured at a previous stage.

The apparatus for K-edge based interior tomography image processing according to the present invention is tomography reconstruction technique using an energy-selective detector, such as a photon counting detector, in order to reconstruct an image inside an ROI.

Unlike a default detector, the energy-selective detector can classify x-rays according to energy. Thus, different material images can be acquired depending on energy.

Using this characteristic, a contrast agent, which is a material with a known value, is injected into an object, and the object is reconstructed using the K-edge of the material.

FIG. 2 shows linear attenuation coefficients of iodine which is frequently used as a contrast agent and another material with respect to x-ray energy.

According to the present invention, the interior of a material is reconstructed using a linear attenuation coefficient of the material that changes depending on the left or right of the K-edge.

As shown in FIG. 3, an apparatus for k-edge based interior tomography image processing according to the present invention includes a projection image acquisition unit 31 configured to acquire projection images of a left area (low energy) and a right area (high energy) near the K-edge using an energy-selective measurement method, a parameter initialization unit 32 configured to initialize several parameters needed for image reconfiguration, an ROI interior reconstruction unit 33 configured to perform reconstruction for image reconfiguration using SART+TV minimization until initial convergence is achieved in order to reconstruct an interior of the ROI, a concentration and correction value calculation unit 34 configured to calculate a concentration α (a ratio of the density of iodine to the total density) and a required correction value β using a linear attenuation coefficient of a contrast agent and a linear attenuation coefficient of blood, which are known, in the acquired and reconstructed image, an image compensation unit 35 configured to compensate for the image by using the correction value (β) calculated by the concentration and correction value calculation unit, an iterative reconfiguration determination unit 36 configured to make a determination for stopping iterative reconfiguration when a maximum number of iterations are achieved or the correction value β converges, and a reconfigured image and concentration output unit 37 configured to output images (a left image (low energy) and a right image (high energy)) obtained using an iterative reconfiguration and compensation method and also output the concentration.

The apparatus for K-edge based interior tomography image processing according to the present invention reconstructs is tomography reconstruction technique using an energy-selective detector, such as a photon counting detector, in order to reconstruct an internal image of an object using an energy-selective detector and the k-edge of the material. The apparatus uses left and right K-edge images (low-energy region and high-energy region).

When a contrast agent is injected into an object, a value L of the contrast agent on the left side and a value R of the contrast agent on the right side can be expressed using Equation 1 below:

$$L = \alpha I_L + (1-\alpha) B_L$$

$$R = \alpha I_R + (1-\alpha) B_R \qquad \text{[Equation 1]}$$

A contrast agent is mainly introduced into a blood vessel, and thus the contrast agent and a material (e.g., blood) other than the contrast agent are present in the blood vessel.

Here, $I_L$ is a left linear attenuation coefficient of the contrast agent, $B_L$ is a left linear attenuation coefficient of the blood, $I_R$ is a right linear attenuation coefficient of the contrast agent, and $B_R$ is a right linear attenuation coefficient of the blood.

The image values (i.e., linear attenuation coefficients) are determined by a density ratio between the contrast agent and the blood.

The apparatus for k-edge based interior tomography image processing according to the present invention applies a method of compensating for an internal value of a material in order to solve a problem of an interior of an object not accurately being reconstructed when the object is reconstructed.

As one method of compensating for the internal value of the material, there is a multiplicative method in which an image reconstruction process is performed by multiplying a known value of the material and a value acquired through the image reconstruction.

As another method of compensating for the internal value of the material, there is an additive method in which an image reconstruction process is performed by adding a known value of the material and a value acquired through the image reconstruction so that the sum may be adjusted to a known value.

First, a method of obtaining a correction value for compensating for the internal value of the material in the multiplicative method will be described as follows.

A left intermediate value $M_L$ and a right intermediate value $M_R$ are obtained using a linear attenuation coefficient of a contrast agent and a linear attenuation coefficient of blood, which are known, in a reconfigured image obtained during a process of performing reconstruction for image reconfiguration using SART+TV minimization until initial convergence is achieved in order to reconstruct an interior of the ROI, as expressed using Equation 2 below:

$$M_L = \frac{L}{\beta_m} = \frac{\alpha}{\beta_m} I_L + \frac{(1-\alpha)}{\beta_m} B_L \quad \text{[Equation 2]}$$

$$M_R = \frac{R}{\beta_m} = \frac{\alpha}{\beta_m} I_R + \frac{(1-\alpha)}{\beta_m} B_R$$

The concentration $\alpha$ and the correction value $\beta_m$ obtained in the multiplicative method can be expressed using Equation 3 below:

$$\alpha = \frac{M_L B_R - M_R B_L}{M_L(B_R - I_R) - M_R(B_L - I_L)} \quad \text{[Equation 3]}$$

$$\beta_m = \frac{B_L(I_R - B_R) - B_R(I_L - B_L)}{M_L(I_R - B_R) - M_R(I_L - B_L)}$$

Next, a method of obtaining a correction value for compensating for the internal value of the material in the additive method will be described as follows.

A left intermediate value $M_L$ and a right intermediate value $M_R$ are obtained using a linear attenuation coefficient of a contrast agent and a linear attenuation coefficient of blood, which are known, from a reconfigured image obtained during a process of performing reconstruction for image reconfiguration using SART+TV minimization until initial convergence is achieved in order to reconstruct an interior of the ROI, as expressed using Equation 4 below:

$$M_L = L + \beta_\alpha = \alpha I_L + (1-\alpha) B_L + \beta_\alpha$$

$$M_R = R + \beta_\alpha = \alpha I_R + (1-\alpha) B_R + \beta_\alpha \quad \text{[Equation 4]}$$

The concentration $\alpha$ and the correction value $\beta_\alpha$ obtained in the additive method can be expressed using Equation 5 below:

$$\alpha = \frac{(M_L - M_R) - (B_L - B_R)}{(I_L - I_R) - (B_L - I_R)} \quad \text{[Equation 5]}$$

$$\beta_\alpha = \frac{(M_L - B_L)(I_R - B_R) - (M_R - B_R)(I_L - B_L)}{(I_R - B_R) - (I_L - B_L)}$$

Also, total variation (TV) minimization, which is a method capable of accurate reconstruction in a sparsity model, is used for the image reconstruction.

A method for K-edge based interior tomography image processing according to the present invention will be described in detail below.

Figure 4:
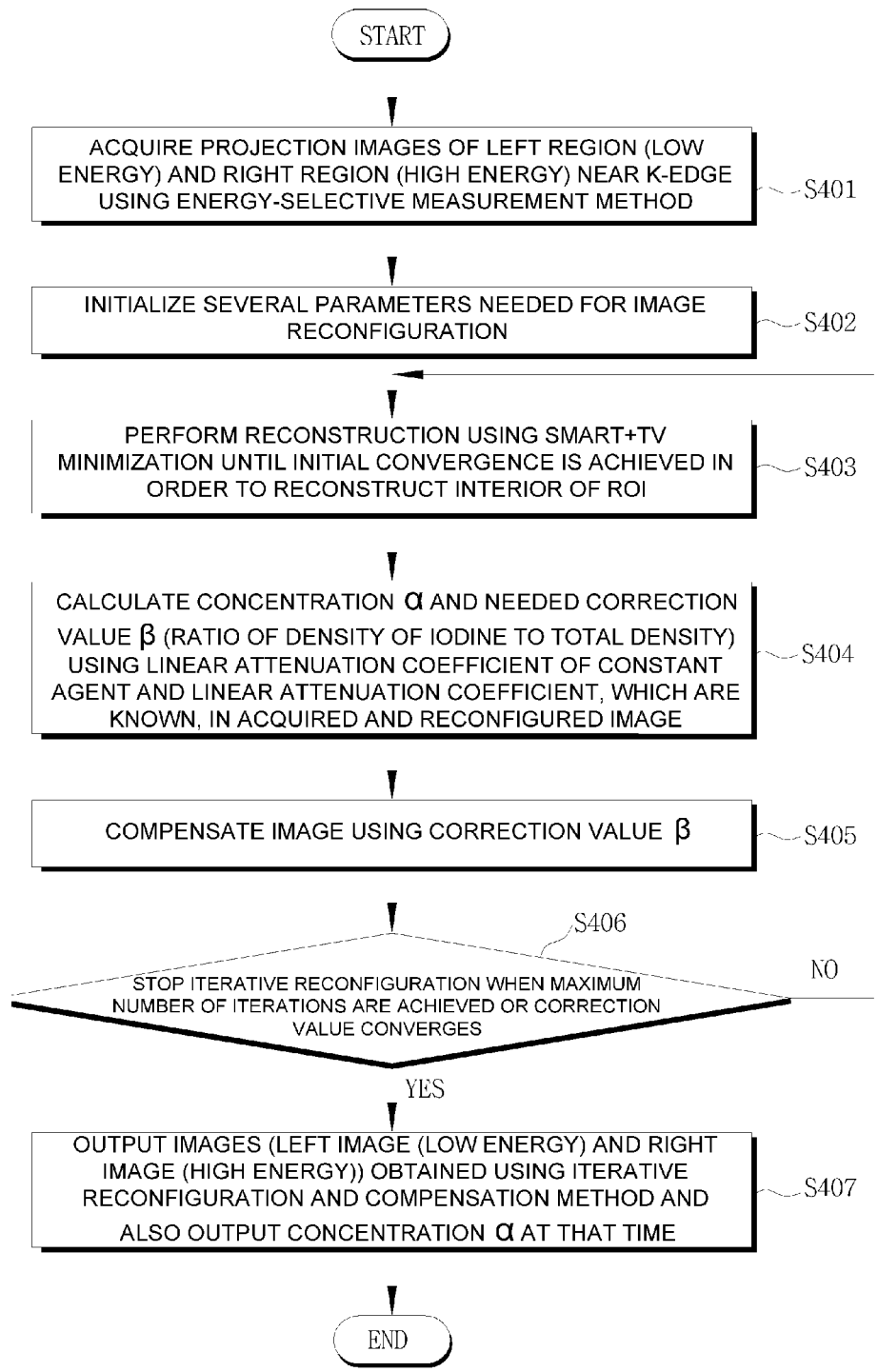
FIG. 4 is a flowchart showing a method for K-edge based interior tomography image processing according to the present invention.

FIG. 4 is a flowchart showing a method for K-edge based interior tomography image processing according to the present invention.

First, a projection image acquisition unit 31 acquires projection images of a left area (low energy) and a right area (high energy) near the K-edge using an energy-selective measurement method (S401).

Next, a parameter initialization unit 32 initializes several parameters needed for image reconfiguration (S402).

An ROI interior reconstruction unit 33 performs reconstruction for image reconfiguration using SART+TV minimization until initial convergence is achieved in order to reconstruct an interior of the ROI (S403).

Next, a concentration and correction value calculation unit 34 calculates a concentration $\alpha$ (a ratio of the density of iodine to the total density) and a required correction value $\beta$ using a linear attenuation coefficient of a contrast agent and a linear attenuation coefficient of blood, which are known, in the reconstructed image acquired by the concentration and correction value calculation unit 34 (S404).

Also, an image compensation unit 35 compensates for the image by using the correction value ($\beta$) calculated by the concentration and correction value calculation unit (S405).

Next, an iterative reconfiguration determination unit 36 performs determination for stopping iterative reconfiguration when a maximum number of iterations are achieved or the correction value $\beta$ converges (S406).

A reconfigured image and concentration output unit 37 outputs images (a left image (low energy) and a right image (high energy)) obtained using an iterative reconfiguration and compensation method and also outputs concentrations at that time.

A result of the method for K-edge based interior tomography image processing according to the present invention is shown in Table 1 below.

TABLE 1

|  | Left | Right |
| --- | --- | --- |
| Value of the marker | IL: 5 | IR: 5.1 |
| Value of the background | 0.35 | |
| Concentration | 0.01 | |

Here, "Value of the background" indicates a linear attenuation coefficient of blood in a blood vessel including a contrast agent.

Figure 5:
FIG. 5 shows a phantom that was used for K-edge based interior tomography image processing according to the present invention.

FIG. 5 shows a phantom that was used for K-edge based interior tomography image processing according to the present invention, and FIG. 6 shows an image configuration diagram obtained through K-edge based interior tomography image processing according to the present invention.

FIGS. 6A through 6D show a result of internal tomography image reconfiguration. A portion (FIG. 6A) shows filtered backprojection, a portion (FIG. 6B) shows a result of conventional interior tomography, a portion (FIG. 6C) shows a result of image reconfiguration through compensation using the multiplicative method according to the present invention, and a portion (FIG. 6D) shows a result of image reconfiguration through compensation using the additive method according to the present invention.

Figure 7:
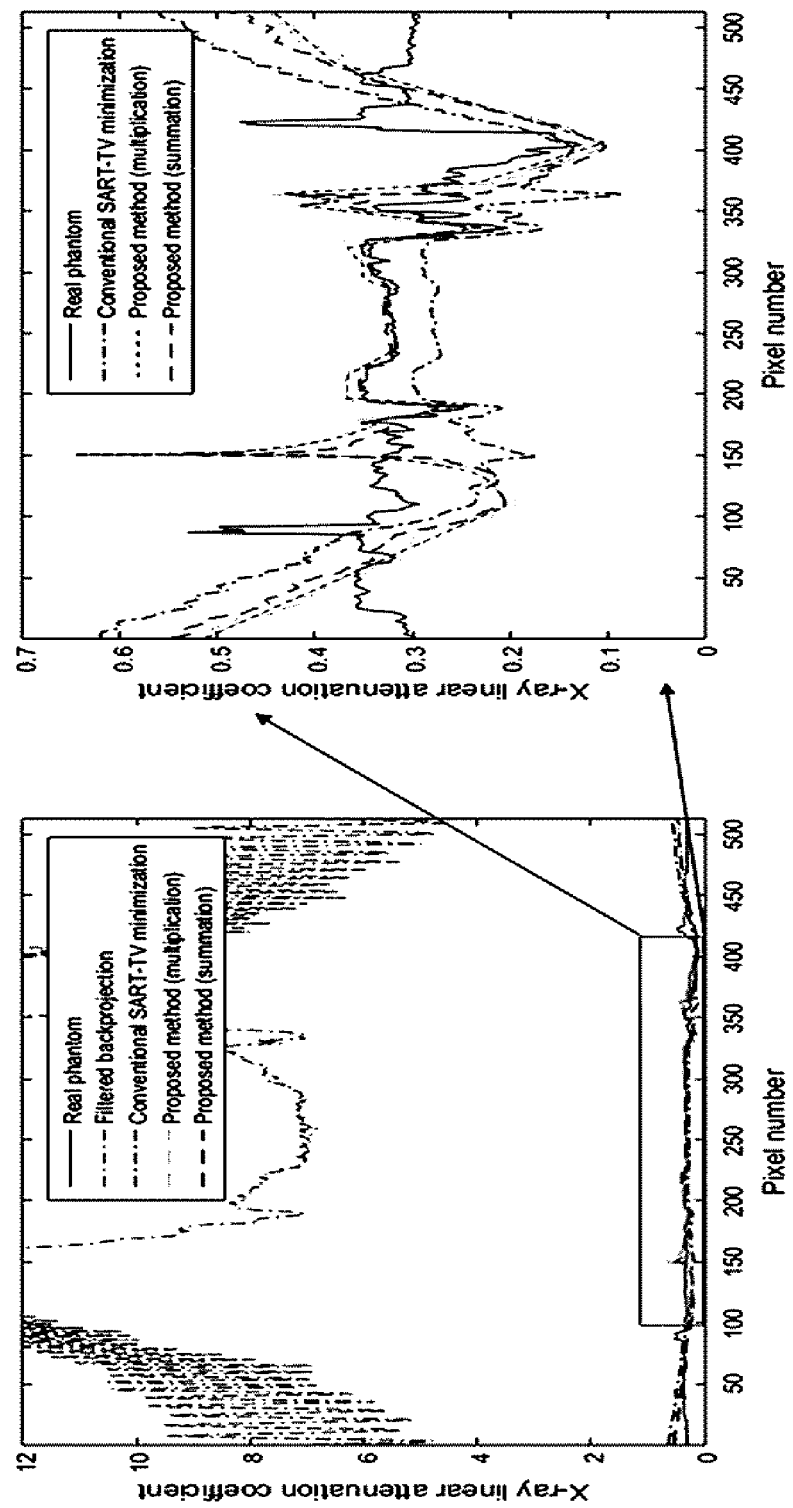
FIG. 7 shows graphs of image reconfiguration characteristics obtained through K-edge based interior tomography image processing according to the present invention.

FIG. 7 shows graphs of image reconfiguration characteristics obtained through K-edge based interior tomography image processing according to the present invention.

It can be seen that image reconfiguration characteristics obtained through K-edge based interior tomography image processing according to the present invention are better than those of the conventional method.

It can be seen that it is possible to more accurately reconfigure an image of an ROI in a system and perform the reconfiguration even when there is no known area (sub-region) in the ROI.

According to the above-described apparatus and method for K-edge based interior tomography image processing according to the present invention, it is possible to efficiently reconstruct a computed tomography (CT) image by acquiring different material images using an energy-selective detector, such as a photon counting detector capable of classifying x-rays according to energy.

The present invention uses left and right K-edge images (low-energy region and high-energy region) in order to reconstruct an internal image of an object using an energy-selective detector and a K-edge of the object. According to the present invention, it is possible to increase image reconfiguration performance by performing image reconstruction while performing multiplication of a ratio between the known value of the material and a value acquired through the image reconstruction, and compensate for an internal value of the object or while performing addition of a difference between the known value of the material and the value acquired through the image reconstruction and adjusting the sum to a known value.

The K-edge based interior tomography image processing apparatus and method according to the present invention have the following effects.

First, it is possible to efficiently perform tomography image reconstruction by acquiring different material images using an energy-selective detector, such as a photon counting detector capable of classifying x-rays according to energy.

Second, it is possible to enhance image reconfiguration performance by reconstructing an internal image of an object using an energy-selective detector and images on both sides of a K-edge of a material (low-energy region and high-energy region).

Third, it is possible to enhance image reconfiguration performance by injecting a material (contrast agent) with a known value into an object, reconstructing an interior of the object using a linear attenuation coefficient of the material that changes depending on a left or right side of a K-edge, performing multiplication of a ratio between the known value of the material and a value acquired through the image reconstruction, and compensating for an internal value of the object.

Fourth, it is possible to enhance image reconfiguration performance by injecting a material (contrast agent) with a known value into an object, reconstructing an interior of the object using a linear attenuation coefficient of the material that changes depending on a left or right side of a K-edge, performing addition of a difference between the known value of the material and a value acquired through the image reconstruction, and adjusting the sum to a known value to perform the image reconstruction.

Fifth, it is possible to accurately reconfigure an image of a region of interest (ROI) in a system and also perform the reconfiguration even when there is no known area (sub-region) in the ROI.

Hereinabove, it will be understood that present invention may be implemented in a modified form without departing from essential characteristics of the present invention.

Therefore, the exemplary embodiments disclosed herein should be considered in an illustrative sense rather than in a restrictive sense. The scope of the present invention should be defined not by the detailed description but by the appended claims, and all differences within the scope should be construed as being included in the present invention.

What is claimed is:

1. An apparatus for K-edge based interior tomography image processing, the apparatus comprising:
a projection image acquisition unit configured to inject a contrast agent into an object and acquire projection images using an energy-selective measurement with respect to a K-edge;
a parameter initialization unit configured to initialize parameters needed for image reconfiguration;
an ROI interior reconstruction unit configured to perform reconstruction for image reconfiguration until initial convergence is achieved in order to reconstruct an interior of a region of interest (ROI);
a concentration and correction value calculation unit configured to calculate a concentration and a correction value ($\beta$) using a linear attenuation coefficient of the contrast agent and a linear attenuation coefficient of blood, which are known, in an acquired and reconstructed image;
an image compensation unit configured to compensate for the image by using the correction value ($\beta$) calculated by the concentration and correction value calculation unit;
an iterative reconfiguration determination unit configured to make a determination for stopping iterative reconfiguration when a maximum number of iterations are achieved or the correction value ($\beta$) converges; and
a reconfigured image and concentration output unit configured to output a resultant image obtained using iterative reconfiguration and compensation and also output a concentration ($\alpha$);
wherein when the contrast agent is injected into the object, a contrast agent value (L) on a left side of the K-edge and a contrast agent value (R) on a right side of the K-edge are calculated using the following equations:

$$L = \alpha I_L + (1-\alpha) B_L$$

$$R = \alpha I_R + (1-\alpha) B_R$$

where $I_L$, is a linear attenuation coefficient of the contrast agent on the left side of the K-edge, $B_L$ is a linear attenuation coefficient of the blood on the left side of the K-edge, $I_R$ is a linear attenuation coefficient of the contrast agent on the right side of the K-edge, and $B_R$ is a linear attenuation coefficient of the blood on the right side of the K-edge.

2. The apparatus of claim 1, wherein the projection image acquisition unit uses a photon counting detector in order to acquire the projection images with respect to the K-edge using the energy-selective measurement.

3. The apparatus of claim 1, wherein a linear attenuation coefficient, which is an image value, is determined by a density ratio between the contrast agent and the blood.

4. The apparatus of claim 1, wherein the contrast agent is iodine having a K-edge at an energy value of 33.2 keV or barium having a K-edge at an energy value of 37.4 keV.

5. The apparatus of claim 1, wherein the ROI interior reconstruction unit performs reconstruction for image reconfiguration using SART+TV minimization until initial convergence is achieved in order to reconstruct the interior of the ROI.

6. The apparatus of claim 1, wherein the reconfigured image and concentration output unit outputs a left K-edge image obtained by imaging a low-energy area and a right K-edge image obtained by imaging a high-energy area with respect to the K-edge, which is an energy boundary at which there is an increase in the linear attenuation coefficient.

7. The apparatus of claim 1, wherein the image compensation unit reconstructs an interior of the object using a linear attenuation coefficient of a material that changes depending on a left or right side of the K-edge.

8. A method for K-edge based interior tomography image processing, the method comprising:
a projection image acquisition operation of injecting a contrast agent into an object and acquiring projection images using an energy-selective measurement with respect to a K-edge;
a parameter initialization operation of initializing parameters needed for image reconfiguration;
an ROI interior reconstruction operation of performing reconstruction for image reconfiguration until initial convergence is achieved in order to reconstruct an interior of a region of interest (ROI);
a concentration and correction value calculation operation of calculating a concentration and a correction value ($\beta$) using a linear attenuation coefficient of the contrast agent and a linear attenuation coefficient of blood, which are known, in the acquired and reconstructed image;
an image compensation operation of compensating for the image by using the calculated correction value ($\beta$);
an iterative reconfiguration determination operation of making a determination for stopping iterative reconfiguration when a maximum number of iterations are achieved or the correction value ($\beta$) converges; and
a reconfigured image and concentration output operation of outputting a resultant image obtained using iterative reconfiguration and compensation and also outputting a concentration ($\alpha$);
wherein when the contrast agent is injected into the object, a value (L) of the contrast agent on a left side and a value (R) of the contrast agent on a right side are calculated using the following equations:

$L = \alpha I_L + (1-\alpha) B_L$ $R = \alpha I_R + (1-\alpha) B_R$ where $I_L$ is a left linear attenuation coefficient of the contrast agent, $B_L$ is a left linear attenuation coefficient of the blood, $I_R$ is a right linear attenuation coefficient of the contrast agent, and $B_R$ is a right linear attenuation coefficient of the blood.

9. The method of claim 8, wherein the ROI interior reconstruction operation comprises reconstruction for image reconfiguration using SART+TV minimization until initial convergence is achieved in order to reconstruct the interior of the ROI.

10. The method of claim 8, wherein the reconfigured image and concentration output operation comprises outputting a left K-edge image obtained by imaging a low-energy area and a right K-edge image obtained by imaging a high-energy area with respect to the K-edge, which is an energy boundary at which there is an increase in the linear attenuation coefficient.

11. The method of claim 8, wherein the image compensation operation comprises compensating for an internal value of the object by reconstructing an interior of the object using a linear attenuation coefficient of a material that changes depending on a left or right side of the K-edge.

12. The method of claim 11, wherein in the image compensation operation, a concentration ($\alpha$) and a correction value ($\beta_m$) are calculated using the following equations:

$$\alpha = \frac{M_L B_R - M_R B_L}{M_L(B_R - I_R) - M_R(B_L - I_L)}$$

$$\beta_m = \frac{B_L(I_R - B_R) - B_R(I_L - B_L)}{M_L(I_R - B_R) - M_R(I_L - B_L)}$$

where $M_L$ is a left intermediate value in a process of performing the reconstruction for image reconfiguration, $M_R$ is a right intermediate value, $I_L$ is a linear attenuation coefficient of the contrast agent on the left side of the K-edge, $B_L$ is a linear attenuation coefficient of the blood on the left side of the K-edge, $I_R$ is a linear attenuation coefficient of the contrast agent on the right side of the K-edge, and $B_R$ is a linear attenuation coefficient of the blood on the right side of the K-edge.

13. The method of claim 8, wherein the image compensation operation comprises reconstructing an interior of the object using a linear attenuation coefficient of the material that changes depending on a left or right side of the K-edge.

14. The method of claim 13, wherein in the image compensation operation, a concentration ($\alpha$) and a correction value ($\beta_\alpha$) calculated using the following equations:

$$\alpha = \frac{(M_L - M_R) - (B_L - B_R)}{(I_L - I_R) - (B_L - I_R)}$$

$$\beta_\alpha = \frac{(M_L - B_L)(I_R - B_R) - (M_R - B_R)(I_L - B_L)}{(I_R - B_R) - (I_L - B_L)}$$

where $M_L$ is a left intermediate value in a process of performing the reconstruction for image reconfiguration, $M_R$ is a right intermediate value, $I_L$ is a linear attenuation coefficient of the contrast agent on the left side of the K-edge, $B_L$ is a linear attenuation coefficient of the blood on the left side of the K-edge, $I_R$ is a linear attenuation coefficient of the contrast agent on the right side of the K-edge, and $B_R$ is a linear attenuation coefficient of the blood on the right side of the K-edge.

* * * * *